(12) United States Patent
Nishigaki

(10) Patent No.: US 10,191,074 B2
(45) Date of Patent: Jan. 29, 2019

(54) AUTOMATIC ANALYZING APPARATUS

(71) Applicant: Hitachi High-Technologies Corporation, Tokyo (JP)

(72) Inventor: Kenichi Nishigaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 72 days.

(21) Appl. No.: 15/324,289

(22) PCT Filed: Jul. 6, 2015

(86) PCT No.: PCT/JP2015/069371
§ 371 (c)(1),
(2) Date: Jan. 6, 2017

(87) PCT Pub. No.: WO2016/009862
PCT Pub. Date: Jan. 21, 2016

(65) Prior Publication Data
US 2017/0227563 A1    Aug. 10, 2017

(30) Foreign Application Priority Data

Jul. 18, 2014    (JP) .................................. 2014-147287

(51) Int. Cl.
G01N 35/10    (2006.01)
G01N 35/02    (2006.01)
G01R 29/24    (2006.01)
G01N 21/77    (2006.01)

(52) U.S. Cl.
CPC ....... *G01N 35/1004* (2013.01); *G01N 35/025* (2013.01); *G01N 35/1002* (2013.01); *G01R 29/24* (2013.01); *G01N 21/77* (2013.01)

(58) Field of Classification Search
None
See application file for complete search history.

(56) References Cited

U.S. PATENT DOCUMENTS

2007/0148042 A1    6/2007    Ootani et al.
2012/0051975 A1*   3/2012    Buffiere ............ G01N 35/1079
                                                            422/68.1

FOREIGN PATENT DOCUMENTS

JP          06-18968 U        3/1994
JP          11-271319 A       10/1999
JP          2008-215931 A     9/2008
(Continued)

OTHER PUBLICATIONS

English translation of Ishibashi, Toru Liquid Sample Dispensing Device, and Biochemical Reaction Device Equipped With Same (Mar. 18, 2008). (Year: 2008).*

(Continued)

*Primary Examiner* — Kathryn Wright
(74) *Attorney, Agent, or Firm* — Mattingly & Malur, PC

(57) ABSTRACT

An automatic analyzing apparatus capable of eliminating static electricity charged in a specimen container at a specimen dispensing position provided. The automatic analyzing apparatus includes a dispensing mechanism having a probe that aspirates a liquid and an arm that holds the probe, and a static eliminator having a generation source of neutralizing ions and a neutralizing ion blowing mechanism for blowing the neutralizing ions generated in the generation source to a target, which are provided in the dispensing mechanism.

8 Claims, 10 Drawing Sheets

(56) References Cited

FOREIGN PATENT DOCUMENTS

JP     2008-267830 A     11/2008
JP     2009-030987 A     2/2009

OTHER PUBLICATIONS

International Search Report of PCT/JP2015/069371 dated Sep. 15, 2015.
Extended European Search Report received in corresponding European Application No. 15821639.0 dated Feb. 14, 2018.

* cited by examiner

AUTOMATIC ANALYZING APPARATUS

TECHNICAL FIELD

The present invention relates to an automatic analyzing apparatus for performing qualitative and quantitative analysis of a biological sample such as blood and urine, and more particularly to an automatic analyzing apparatus having a system for measuring a light amount of a reaction vessel interposed between a light source and a spectroscopic detector.

BACKGROUND ART

Up to now, as a device for automatically analyzing a specimen such as blood and urine, an analyzing apparatus that dispenses a specimen and one or more kinds of reagents into the reaction vessel to cause a chemical change between the specimen and the reagents, and thereafter measures an absorbance of a reaction solution of the specimen and the reagents to automatically analyze the specimen has been known.

Such an analyzing apparatus suffers from problems such as dust adhering to a container caused by charging of the container in which the specimen is accommodated, creeping up of the liquid on an inner wall of the container, malfunctioning of a liquid level detection, and the like. Also, the same problems arise not only in the specimen container but also in the reaction vessel.

For that reason, up to now, there has been proposed an analyzing apparatus in which an ionizer is installed in the middle of a transfer path of a container containing a liquid and air is blown into the container and around the container to neutralize the container (refer to Patent Literature 1). Also, in order to neutralize the reaction vessel itself, there has been proposed an analyzing apparatus in which a neutralizing device installed on a movement path of a react on vessel exposes the reaction vessel to a neutralizing shower to neutralize electricity (refer to Patent Literature 2).

CITATION LIST

Patent Literature

Patent Literature 1: Japanese Unexamined Patent Application No. 2008-267830
Patent Literature 2: Japanese Unexamined Utility Model Application No. Hei6(1994)-18968

SUMMARY OF INVENTION

Technical Problem

Patent Literature 1 and Patent Literature 2 disclose static eliminators for eliminating static electricity. However, the static eliminators disclosed in Patent Literature 1 and Patent Literature 2 are required to be installed on a traveling route of a specimen container or a reaction vessel. For that reason, because the specimen is charged until the specimen travels to a dispensing position after having passed through the static eliminator, a problem that the static electricity cannot be completely eliminated arises, An object of the present invention is to provide an apparatus for eliminating static electricity at a dispensing position without providing a static eliminator on a traveling route.

Solution to Problem

A representative invention relating to the present application will be described as follows.

An automatic analyzing apparatus includes a dispensing mechanism including a probe that aspirates a liquid and an arm that holds the probe; and a static eliminator having a generation source of neutralizing ions and a neutralizing ion blowing mechanism for blowing neutralizing ions generated in the generation source to a target, which are provided in the dispensing mechanism.

Advantageous Effects of Invention

According to the present invention, the static electricity charged on a traveling or transporting route can be eliminated just before dispensing, and the neutralizing function can be provided without newly providing a static eliminator on the traveling or transporting route.

The problems, configurations, and advantages other than those described above will be clarified from the description of the embodiments below.

DESCRIPTION OF EMBODIMENTS

Hereinafter, embodiments will be described below.

First Embodiment

Figure 1:
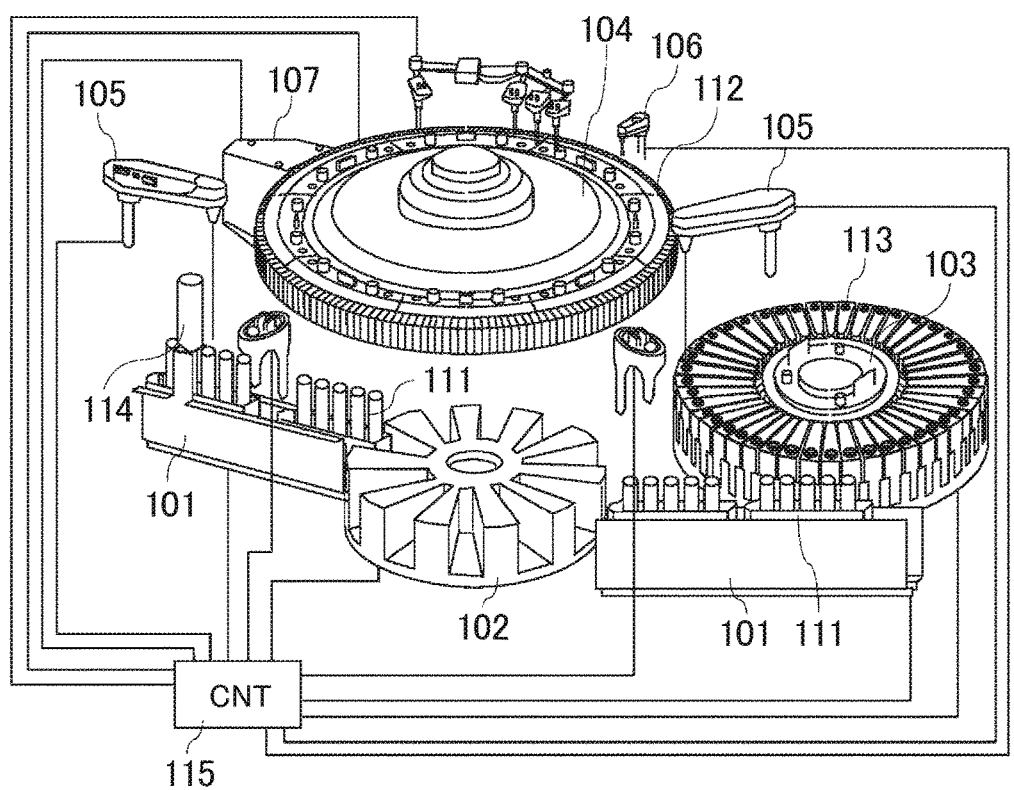
FIG. 1 is a schematic configuration diagram of an automatic analyzing apparatus according to an embodiment of the present invention.

Hereinafter, the present invention will be described according to embodiments in detail.
FIG. 1 is a schematic configuration diagram of an automatic analyzing apparatus according to an embodiment of the present invention.

The automatic analyzing apparatus according to the present embodiment mainly includes a transport line 101, a reaction disk 104, a reagent disk 103, and a spectrometer 107.

Each specimen rack 111 on which specimen containers 110 are installed is transported from a transport line 101 to a rotor 102 and transported to a shield portion 114 as a dispensing position. Thereafter, the specimen necessary for analysis is dispensed to each reaction vessel 112 on a reaction disk 104 by a dispensing mechanism 105. Further, a necessary reagent is dispensed from each reagent container 113 on a reagent disk 103 into the reaction container 112, and a reaction solution is mixed together by a stirring mechanism 106.

The absorbance of the reaction solution is measured with a spectrometer 107. A predetermined component concentration in the specimen is calculated from the measured absorbance and a preliminarily prepared calibration curve. These mechanisms are controlled by a control unit 115. The control unit 115 also calculates the component concentration.

Figure 2:
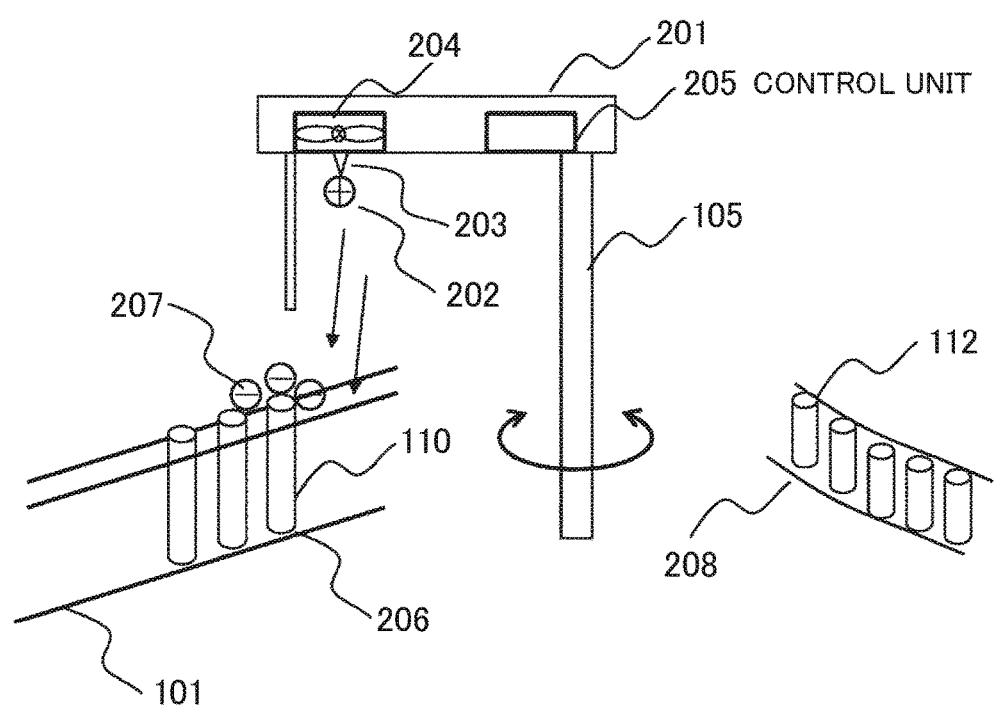
FIG. 2 is a detailed diagram of a static eliminator in the automatic analyzing apparatus according to the present invention.

FIG. 2 is a detailed diagram of a static eliminator in the automatic analyzing apparatus according to the present invention. The automatic analyzing apparatus includes a static eliminator having a dispensing mechanism 105 with a probe for aspirating a liquid and an arm for holding the probe, a generating source for generating neutralizing ions 202 provided in the dispensing mechanism 105, and a neutralizing ion blowing mechanism for blowing the neutralizing ions generated by the generation source to an object. In the present embodiment, the blower fan 204 is employed as the neutralizing ion blowing mechanism.

The static eliminator is incorporated integrally with the dispensing mechanism 105. A discharge needle 203 which is a generation source of the neutralizing ions 202 discharging ions 202, the blower fan 204 for effectively hitting the ions against the object, and a neutralization control unit 205 for controlling those components are installed in an arm 201 of the dispensing mechanism 105. The neutralization control unit 205 controls a power to the discharge needle 203 and the blower fan 204 so as to generate the neutralizing ions from the discharge needle 203 and drive the blower fan 204.

When the specimen containers 110 installed on the apparatus by a user is moved and transported to a dispensing position 206 by the transport line 101, the specimen containers 110 are charged with static electricity 207. After the dispensing mechanism 105 has moved to the dispensing position 206, the neutralizing ions 202 are radiated from the discharge needle 203 according to a command from the neutralization control unit 205, and those neutralizing ions are brought into contact with the specimen containers 110 by the blower fan 204, and the static electricity 207 is electrically neutralized and removed. The dispensing mechanism 105 then performs the dispensing operation of the specimen. For that reason, because the static electricity 207 can be removed just before the dispensing operation, not only the charge of the specimen container occurring before the specimen containers are installed but also the charge of the specimen containers occurring during traveling and transporting can be eliminated together. In the operation, a main control unit and the neutralization control unit 205 in the automatic analyzing apparatus operate in cooperation with each other to perform the dispensing operation and the neutralizing operation in an optimum time.

In addition, because the neutralizing ions can be blown from above each specimen container, an inside of the specimen container can be neutralized.

Further, in the static eliminator according to the present invention, because one dispensing mechanism 105 can perform the neutralizing function in both of the dispensing position 206 of the specimen container 110 and the dispensing position 208 of the reaction container 112, there is no need to install separate static eliminators for the specimen containers and the reaction vessels disclosed in Patent literature 1 or Patent Literature 2, which contributes to a reduction in the cost of the apparatus and a reduction in installation space.

Figure 3:
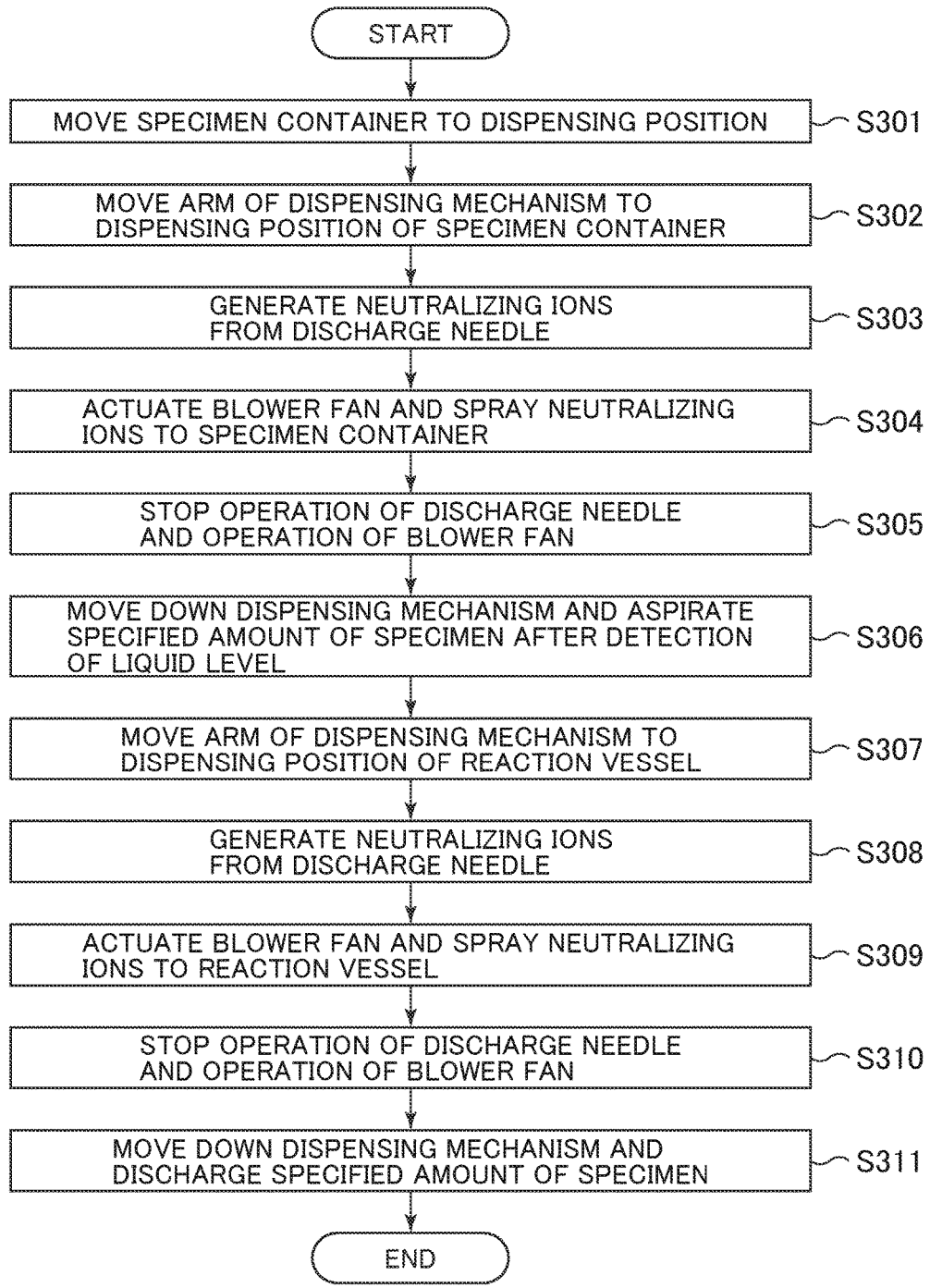
FIG. 3 is a flowchart of the operation of the static eliminator in the automatic analyzing apparatus according to the present invention.

FIG. 3 is a flowchart of the operation of the static eliminator in the automatic analyzing apparatus according to the present invention. The following control is performed by the control unit 115 or the neutralization control unit 205.

After each specimen container installed in the automatic analyzing apparatus by the user have traveled to the dispensing position (S301), the arm of the dispensing mechanism is moved to the dispensing position of the specimen container (S302). Thereafter, the neutralization control unit 205 allows the neutralizing ions to be generated from a discharge needle of the arm above the specimen container (S303) and allows the neutralizing ions generated by activating a blower fan to be sprayed to the specimen container to eliminate static electricity (S304). After the neutralization control unit 205 has stopped the operation of the discharge needle and the operation of the blower fan (S305), the control unit 115 allows the dispensing mechanism to move down toward the specimen container, and aspirate a specified amount of specimen after arrival at a liquid level (S306). The control unit 115 controls the moving-up operation and the horizontal operation of the arm of the dispensing mechanism, and moves the dispensing mechanism to the dispensing position of the reaction vessel (S307). Thereafter, the neutralization control unit 205 allows the neutralizing ions to be generated from the discharging needle (S308), and sprays the neutralizing ions generated by actuating the blower fan to the reaction vessel to eliminate the static electricity S309). After the neutralization control unit 205 has stopped the operation of the discharge needle and the operation of the blower fan (S310), the control unit 115 allows the dispensing mechanism to move down toward the reaction vessel and discharge the aspirated specimen by a specified amount (S311).

In such a way, the static eliminator can neutralize the specimen container and the reaction vessel.

Further, the operation of the discharging needle is stopped to prevent the neutralizing ions from being generated before moving down the dispensing mechanism, as a result of which the malfunction of the liquid level detection caused by the neutralizing ions can be suppressed. This is because the liquid level detection is a mechanism for detecting whether a tip of the probe has come into contact with the liquid level or not, with the detection of a change in a capacitance at the tip of the probe.

In addition, the operation of the blower fan is stopped before moving down the dispensing mechanism, as a result of which a reduction in the dispending precision due to vibrations caused by the operation of the sending fan can be suppressed. In other words, preferably, the neutralization control unit 205 for controlling the generation source of the neutralizing ions and the neutralizing ion blowing mechanism neutralizes the container containing the liquid before the dispensing mechanism moves down. While the dispensing mechanism is moving down, the neutralization control unit 205 stops at least the neutralizing ion blowing mechanism and the probe aspirates the liquid in a state where the neutralizing ion blowing mechanism is stopped.

Meanwhile, in the present embodiment, an example in which the neutralization control unit 205 is included in the dispensing mechanism is shown. However, the static eliminator having the neutralizing ion generation source and the neutralizing ion blowing mechanism for blowing the neutralizing ions toward the object has only to be installed in the dispensing mechanism. Therefore, the neutralization control unit 205 may be located outside the dispensing mechanism.

Second Embodiment

Figure 4:
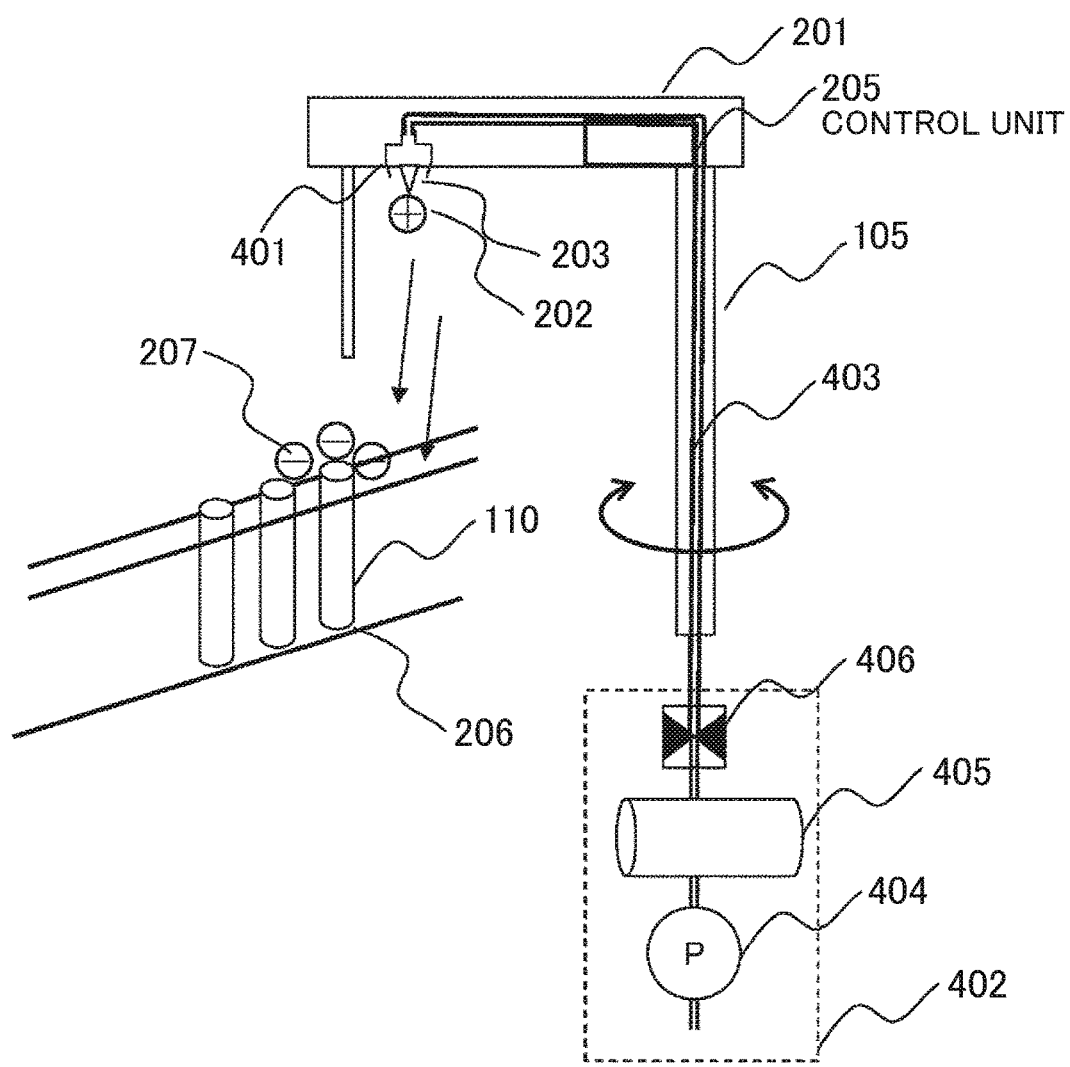
FIG. 4 is a detailed diagram of the static eliminator in the automatic analyzing apparatus according to the present invention.

FIG. 4 is a detailed diagram of the static eliminator in the automatic analyzing apparatus according to the present invention. The present embodiment shows an example in which an air tube 403 for blowing compressed air generated from a compressed air generation unit 402 is employed as the neutralizing ion blowing mechanism.

A static eliminator is incorporated integrally with the dispensing mechanism 105. A discharge needle 203 which is a generation source of a neutralizing ions 202 discharging ions 202 and an air nozzle 401 that can discharge compressed air for the purpose of effectively applying the neutralizing ions 202 to an object. A compressed air generation unit 402 is installed in the automatic analyzing apparatus, and the air nozzle 401 is connected to the compressed air generation unit 402 through an air tube 403 arranged in a support column of the dispensing mechanism 105. The compressed air generation unit 402 includes an air pump 404, a compressed air tank 405, and a solenoid valve 406.

The air pump 404 takes in outside air, sends compressed air to the compressed air tank 405, and keeping a constant air pressure of the compressed air tank 405 at all times.

As in the first embodiment, after a specimen container 110 is moved and transported to a dispensing position 206, the neutralizing ions 202 are radiated from the discharge needle 203 in response to a command from the neutralization control unit 205, and at the same time, a solenoid valve 406 is opened to discharge the compressed air from the air nozzle 401, thereby applying the neutralizing ion 202 to the specimen container 110 to remove static electricity 207.

In the first embodiment, the neutralizing ions 202 are discharged by the aid of a blower fan 204, but in the present embodiment, because weight components such as a fan motor are not included in the arm 201 of the dispensing mechanism 105, the weight of the arm 201 is reduced. Further, in general, due to vibration caused by an electric motor such as a fan, the vibration is affected on an area closer to a structure of the fan during operation of the fan, and in the example of the first embodiment, in order to prevent a reduction in a dispensing precision caused by the vibration to the dispensing operation, there is a need to wait for a transition to the dispensing operation until the fan rotating due to inertia completely stops after the operation of the fan has been stopped. However, in the present embodiment, because no electric motor causing the vibration is present in the arm 201, the dispensing operation can be performed immediately after the neutralizing operation has been completed. From the above viewpoints, the present embodiment can contribute to higher speed operation of the dispensing mechanism.

Figure 5:
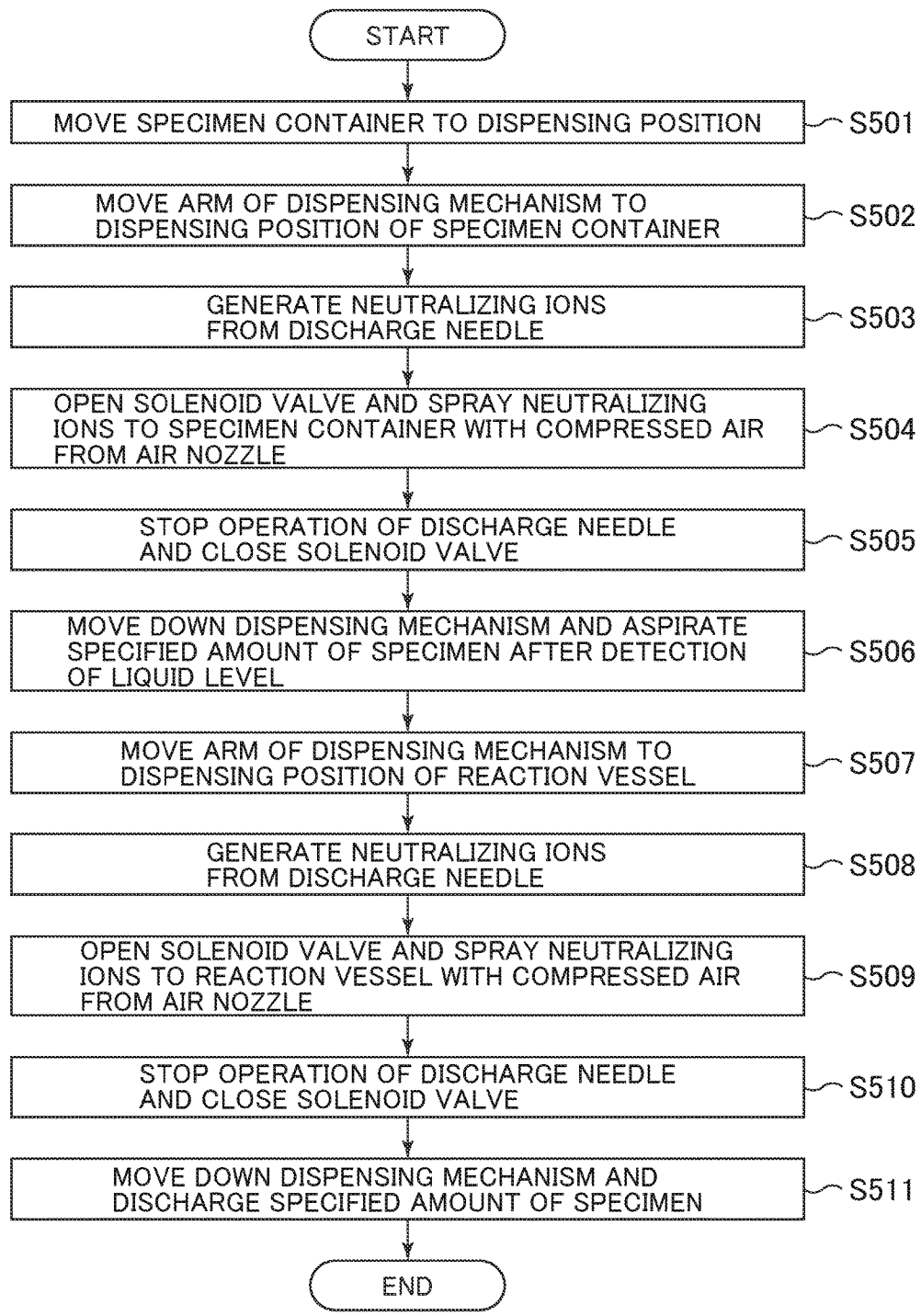
FIG. 5 is a flowchart of the operation in the static eliminator in the automatic analyzing apparatus according to the present invention.

FIG. 5 is a flowchart of the operation in the static eliminator in the automatic analyzing apparatus according to the present invention. The procedure of the neutralization is basically identical with that in the first embodiment.

The difference is a process (S504, 509) of opening the solenoid valve 406 with the use of the compressed air, and a process of closing the solenoid valve 406 (S505, 510). The other processes are the same.

Except for the advantages obtained by replacing the blower with the compressed air generation unit, the other advantages are identical with that in the first embodiment.

Third Embodiment

Figure 6:
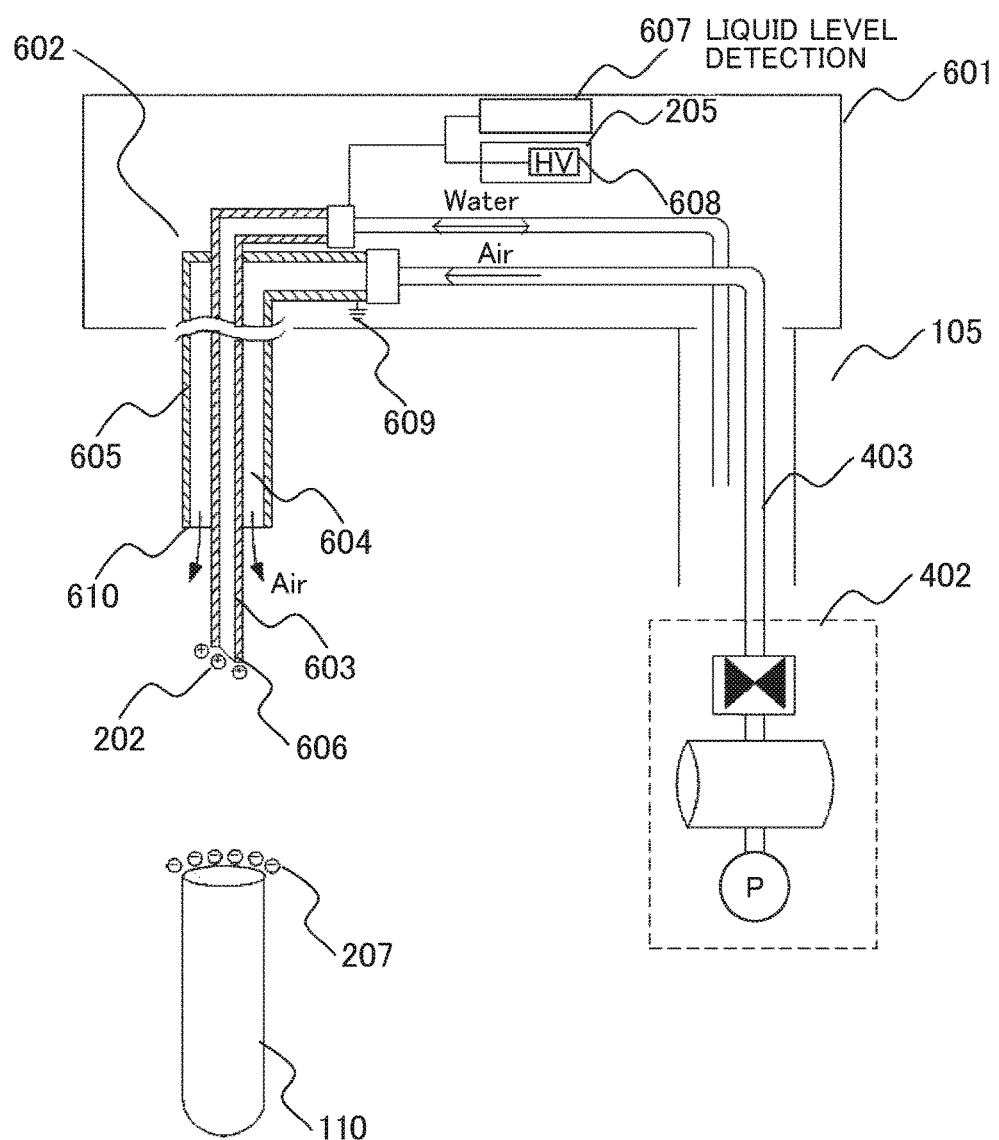
FIG. 6 is a detailed diagram of the static eliminator in the automatic analyzing apparatus according to the present invention.

FIG. 6 is a detailed diagram of the static eliminator in the automatic analyzing apparatus according to the present invention. In the present embodiment, a generation source of neutralizing ions is connected to a probe so that the neutralizing ions can be generated in the probe. In addition, the neutralizing ions are blown to an object by an outer cylinder 605 blowing compressed air generated from the compressed air generation unit.

A static eliminator is incorporated integrally with a dispensing mechanism 105. A dispensing probe 602 with a neutralizing function is installed in an arm 601 of the dispensing mechanism 105. The dispensing probe 602 with the neutralizing function has a function of aspirating and discharging a liquid necessary for a dispensing function, and a static type liquid level detection sensor necessary for detecting a liquid level, as well as a neutralizing function. In other words, the probe is connected to the generation source of the neutralizing ions so that the neutralizing ions can be generated in the probe.

The dispensing probe 602 with the neutralizing function includes a metallic inner cylinder 603 and an outer cylinder 605 provided with a gap 604 through which compressed air can pass so as to surround the inner cylinder 603. The inner cylinder 603 is connected to a flow path such as a syringe, and aspirates and discharges a liquid from an inner cylinder tip 606. Further, the inner cylinder 603 is electrically connected to a liquid surface detection control unit 607, and functions as a liquid level detection sensor with the inner cylinder tip 606 as a detection point with the use of the electrostatic capacitance detection method. Further, the inner cylinder 603 is connected to a high-voltage generator 608 in a neutralization control unit 205, and generates neutralizing ions 202 at the inner cylinder tip 606. The outer cylinder 605 is connected to a ground electrode 609 in order to stabilize a liquid level detection function and is connected to a compressed air generation unit 402 through an air pipe 403 disposed in a support column of a dispensing mechanism 105 to release the compressed air from an outer cylinder tip 610. Further, a control unit such as the neutralization control unit 205 connects an electric connection of the inner cylinder 603 of the dispensing probe to a circuit (liquid level detection circuit) of a liquid level detection control unit, or connects the electric connection to the neutralization control unit. It is desirable to switch the electrical function of the dispensing probe with a switch so that one is enabled and the other is disabled.

As in the second embodiment, after a specimen container 110 is moved and transported to a dispensing position 206, the neutralizing ions 202 are generated from the inner cylinder tip 606 in response to a command from the neutralization control unit 205, and at the same time, a solenoid valve 406 is opened to discharge the compressed air from the outer cylinder tip 610, thereby applying the neutralizing ion 202 to the specimen container 110 to remove static electricity 207.

In the first embodiment and the second embodiment, there is a need to provide the discharge needle 203 for generating the neutralizing ions 202 in the arm 201 of the dispensing mechanism 105. On the other hand, in the present embodiment, the function carried by the discharge needle 203 is integrated by improving the conventional dispensing probe 602, thereby making it unnecessary to separately install the static eliminator, which can contribute to a reduction in an installation space of the static eliminator. In addition, the neutralizing eliminating function is applied to the dispensing probe 602 with neutralizing function itself which is directly affected by the static electricity. As a result, an affected portion and a portion for removing the cause of the influence come as close to each other as possible, which is capable of contributing to effective removal of the static electricity.

Figure 7:
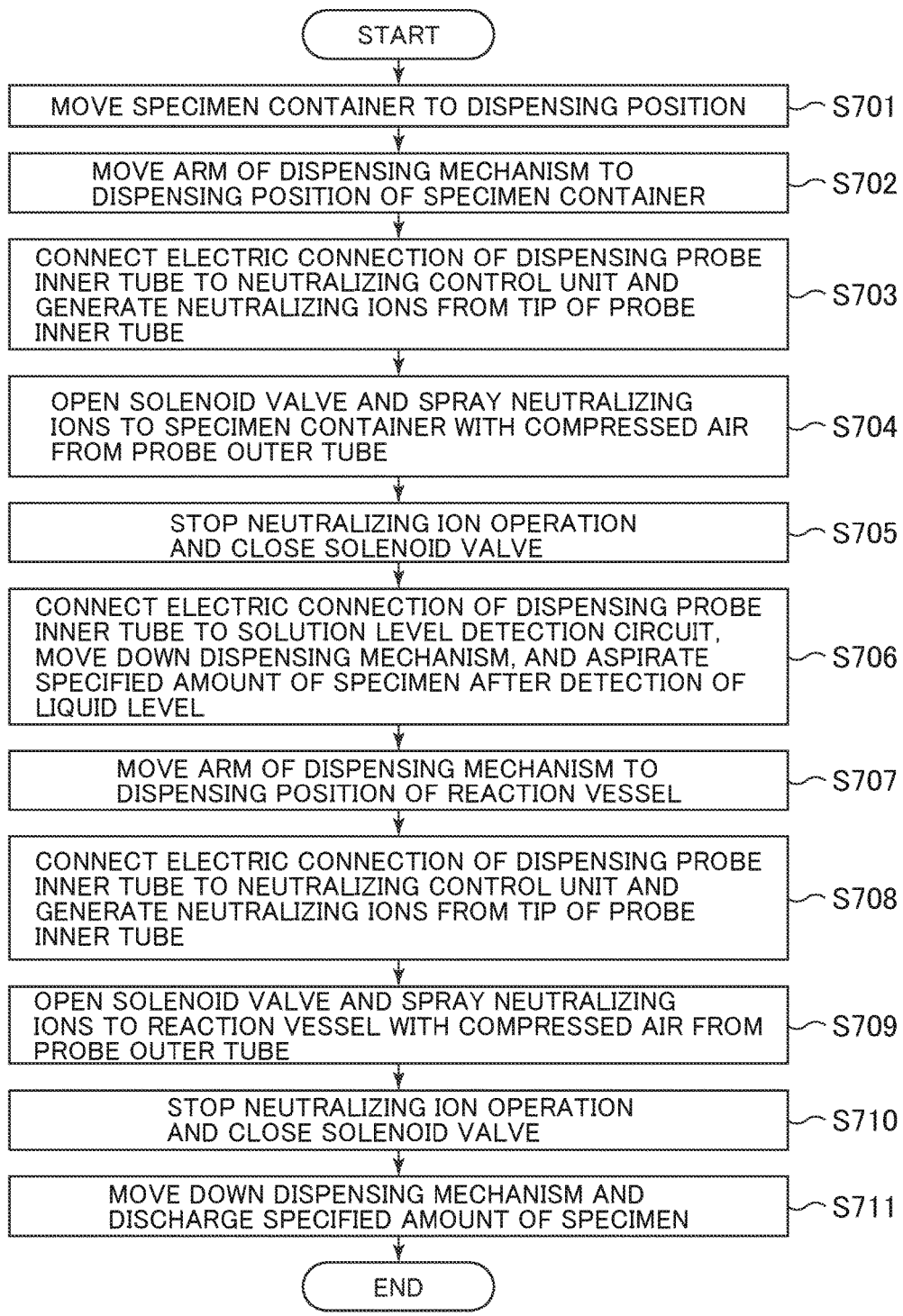
FIG. 7 is a flowchart of the operation in the static eliminator in the automatic analyzing apparatus according to the present invention.

FIG. 7 is a flowchart of the operation in the static eliminator in the automatic analyzing apparatus according to the present invention.

A difference of the present embodiment from the other embodiments resides in that with the use of the dispensing probe as the generation source of neutralizing ions, a connection target is switched to another such that the electrical connection of the dispensing probe inner cylinder is connected to the neutralization unit or connected to the liquid level detection circuit (S703, S706, S708). The other configurations are the same.

The advantages other than those described above are identical with those in the first embodiment.

Fourth Embodiment

Figure 8:
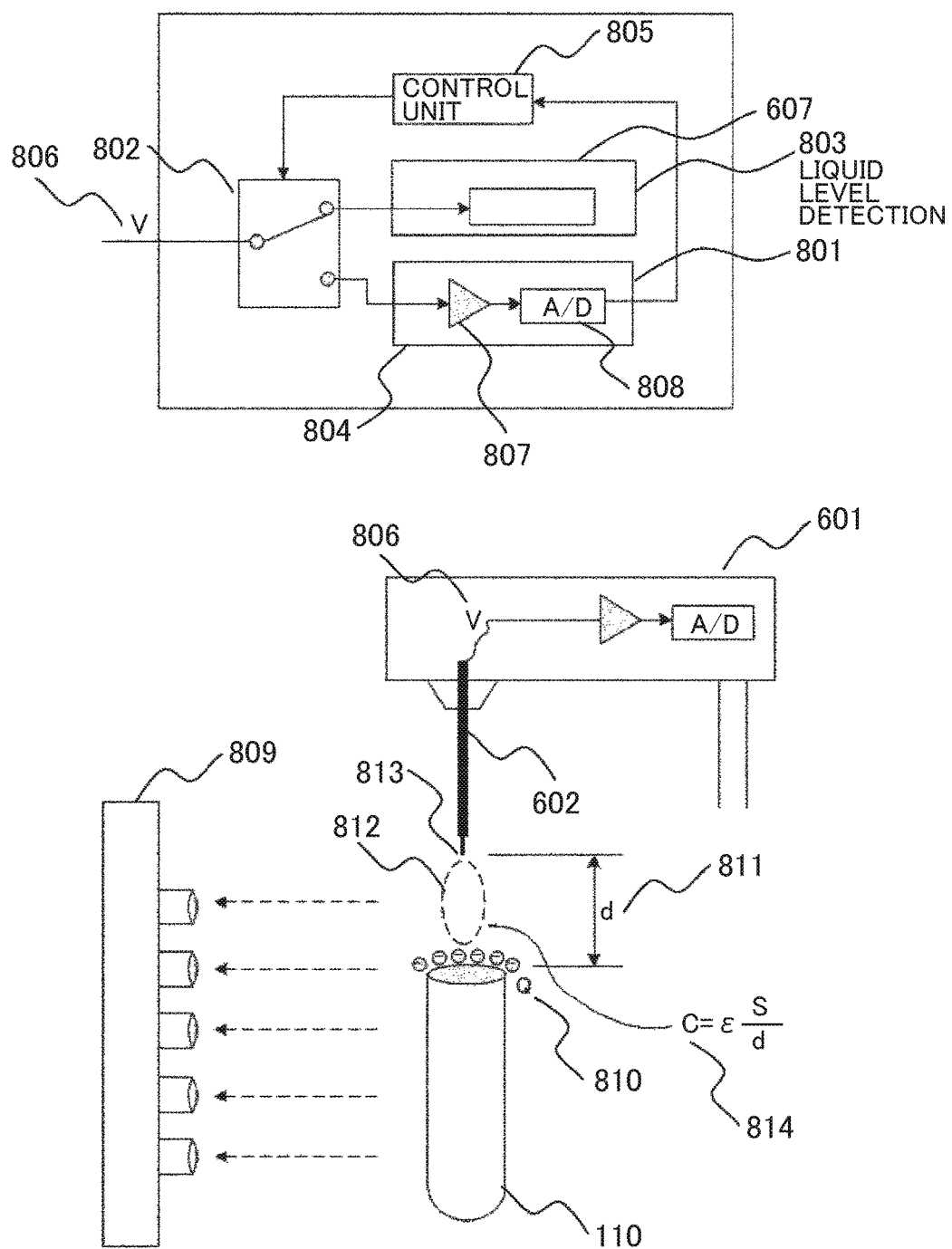
FIG. 8 is a detailed diagram of an accessory function of the static eliminator in the automatic analyzing apparatus according to the present invention.

FIG. 8 is a detailed diagram of an accessory function of the static eliminator in the automatic analyzing apparatus according to the present invention. In the present embodiment, a charge amount measurement unit for measuring an amount of electric charge charged in a specimen container in a non-contact manner with the use of a probe is provided.

In the present embodiment, means for measuring now much electric charge causing static electricity discharge is accumulated in an object such as a specimen container 110 on the basis of the probe 602 with the neutralizing function of the third embodiment is described.

A liquid level detection control unit 607 and a charge amount measurement unit 801 are installed in an arm 601 within a dispensing mechanism 105. In the liquid level detection control unit 607 and the charge amount measurement unit 801, an electric signal is connected from a signal line connected to an inner cylinder 603 of a dispensing probe 602 to a liquid level detection circuit 803 and a charge quantity measurement circuit 804 through an analog switch 802 while being switched by a control unit 805. The charge amount measurement circuit 804 includes an amplifier 807 for amplifying a minute voltage V 806 and an A/D converter 808, and an A/D conversion result of the minute voltage V 806 generated at the tip of the dispensing probe 602 is sent to the control unit 805.

In the automatic analyzing apparatus, a well-known specimen container level detector 809 for detecting a level of the specimen container 110 is mounted.

On a transport line 101 of the automatic analyzing apparatus, the installed specimen containers 110 is moved and transported, and stopped at a dispensing position 206 in the vicinity of a dispensing mechanism 105. The dispensing probe 602 is stopped above the dispensing position 206 to provide a dispensing operation preparation system. An electric charge Q 810 to be static electricity is stored in an opening of the specimen container 110. A distance d811 is provided between the tip portion of the dispensing probe 602 and an opening of the specimen container 110. The distance d811 can be calculated on the basis of a lower descent position of the tip portion of a known dispensing probe 602 and a level of the specimen container obtained from a specimen container level detector 809. Air 812 having a dielectric constant ε is present between the opening of the specimen container 110 and the tip of the dispensing probe 602. It is assumed that a cross-sectional area of the tip of the dispensing probe 602 is S. In this state, an electrostatic capacity C (814) can be calculated on the basis of a dielectric constant ε, a cross-sectional area S (813), and a distance d, and $C=\varepsilon \cdot S/d$ is established. Further, the charge Q (810) can be calculated on the basis of the electrostatic capacitance C (814) and a minute voltage 806 generated at the tip of the dispensing probe 602, from which $Q=C \cdot V$ can be derived.

With the use of the above mechanism, the action of the static eliminator can be adjusted so that the charge Q (810) is sufficiently reduced so as not to discharge the static electricity while checking a reduction of the charge Q 810.

Figure 9:
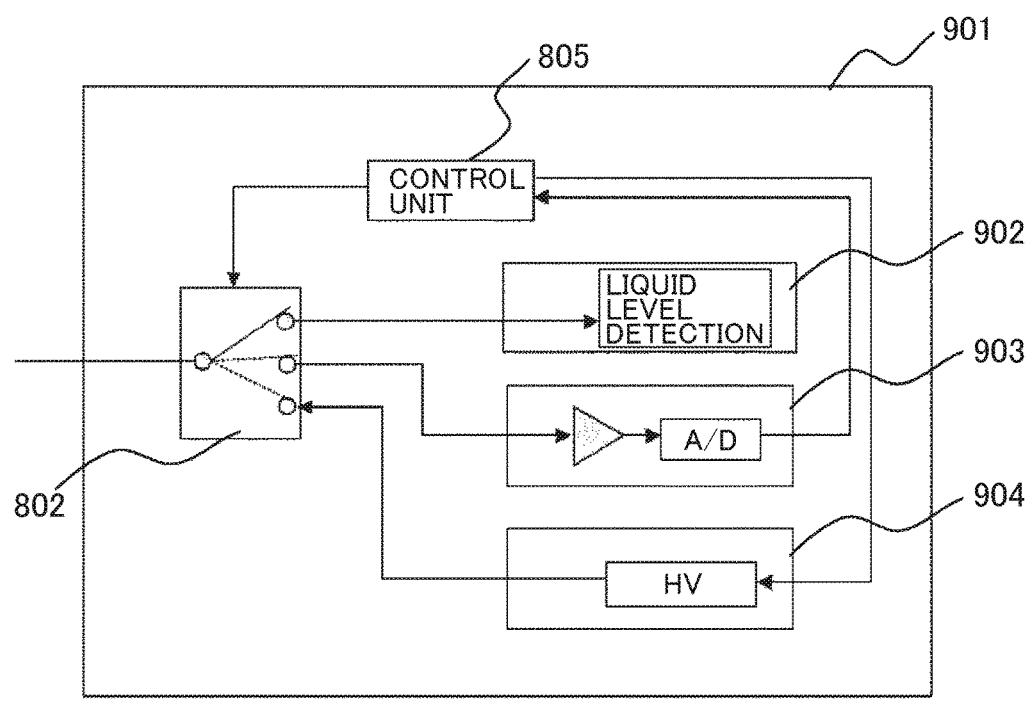
FIG. 9 is a schematic configuration diagram of an integrated neutralizing unit of the automatic analyzing apparatus according to the present invention.

FIG. 9 illustrates an integrated neutralizing unit 901 in which the neutralization control unit 205 is combined with the liquid level detection and the charge amount measurement unit 801. In the integrated neutralizing unit 901, a liquid surface detection unit 902, a charge amount measurement unit 903, a high voltage generation unit 904, and a control unit 805 are provided, and the inner cylinder 603 of the dispensing probe 602 is connected to any circuit through an analog switch 802 switched by the control unit 805. With the combination of those components, before the dispensing operation starts, the dispensing probe 602 is connected to the charge amount measurement unit 903 to measure the electric charge Q 810 accumulated in the opening of the specimen container 110, and the neutralizing ions 202 are discharged from the dispensing probe 602 connected to the high voltage generation unit 904 according to the magnitude of the electric charge Q 810 so as to decrease the charge Q 810. Thereafter, the dispensing probe 602 is switchingly connected to the liquid level detection unit 902, and the dispensing probe 602 is moved down to detect a liquid level of the specimen, thereby being capable of realizing the dispensing function without being affected by the static electricity. As described above, it is desirable to adjust the amount of neutralizing ions to be blown according to the charge amount measured by the charge amount measurement unit. In addition, it is desirable that before the liquid level detection of the specimen accommodated in the specimen container is performed with the use of the probe, it is desirable to measure the amount of electric charge charged in the specimen container by an electrification measurement unit and blow air to the specimen container by the neutralizing ion blowing mechanism. The control is performed by a control unit such as the neutralization control unit or the like.

Figure 10:
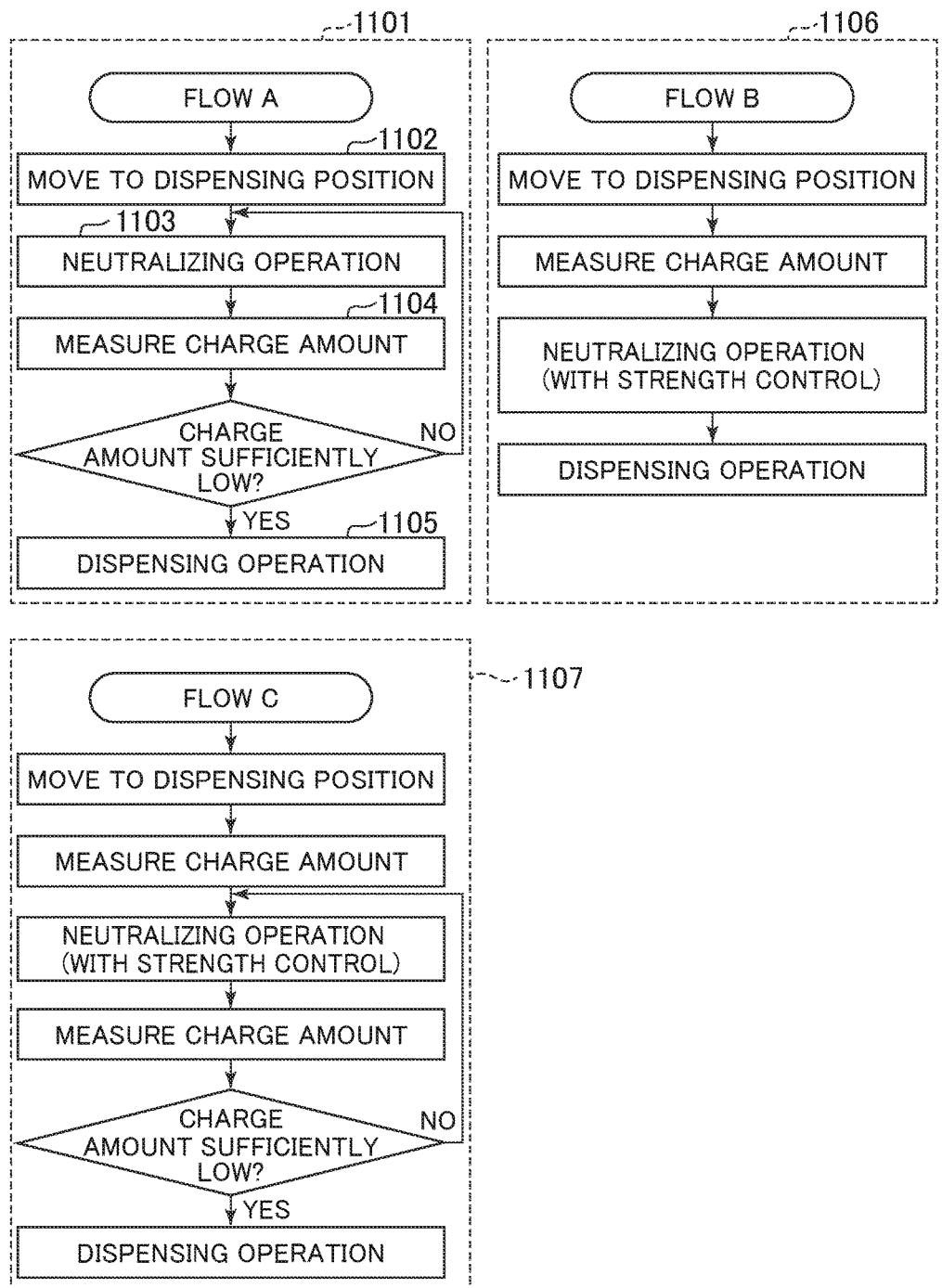
FIG. 10 is a flowchart of neutralizing corresponding to a charge amount according to an embodiment of the present invention.

FIG. 10 illustrates a neutralizing flow according to the amount of electric charge according to an embodiment of the present invention. Multiple neutralizing flows are conceivable according to the combination of operation, and the flow can be selected for an intended purpose such as a high-speed operation version.

In a flow A1101, after the probe has traveled to the dispensing position 1102, the neutralizing operation 1103 is performed. Thereafter, the charge quantity measurement 1104 is performed, and if the amount of electric charge is sufficiently reduced, the dispensing operation 1105 is performed. If the amount of electric charge is not reduced, the neutralizing operation 1103 is again performed.

In a flow B1106, after the probe has traveled to the dispensing position 1102, the charge quantity measurement 1104 is performed. Thereafter, after the neutralizing operation 1103 has been performed according to the amount of electric charge, the dispensing operation 1105 is performed.

In a flow C1107, after the probe has traveled to the dispensing position 1102, the charge quantity measurement 1104 is performed. Thereafter, the neutralizing operation 1103 is performed according to the amount of electric charge. The charge quantity measurement 1104 is again performed, and if the amount of electric charge is sufficiently reduced, the dispensing operation 1105 is performed.

The flow A1101 is useful for a system in which the intensity of neutralization in the neutralizing operation 1103 is fixed and cannot be controlled. The flow B1106 is useful for a system in which the intensity of neutralization in the neutralizing operation 1103 can be controlled, and if it is known that the amount of electric charge is sufficiently reduced in the neutralizing operation 1103, because there is no need to again measure the amount of electric charge, the flow B1106 can perform the fastest operation. The flow C1107 is a flow that can be used by any method irrespective of whether the intensity of neutralization is fixed or controllable, and if the amount of electric charge is sufficiently low from the beginning, a route that does not perform the neutralizing operation is selectable. The flow C1107 can contribute to speeding Lip the neutralizing operation up to the dispensing operation.

The selective use of those flows may be freely set by the user. Since it is difficult for static electricity to be charged originally when used in an environment with high humidity, it is possible to utilize the flow C1107 with an improvement in the processing capability. In other words, in order to enable those flows to be selectively used, it is desirable to provide a display unit capable of selecting a function or the combination of functions to be used by the user from among the liquid level detection function, the charge amount measurement amount, and the static elimination function.

In the present embodiment, the description has been made based on the third embodiment. However, the configuration of the first and second embodiments may be employed for the neutralizing ion blowing mechanism.

As described above, in the embodiment, the racks are employed for transporting the specimen container, but the static eliminator according to the present invention is effective even when the specimen disk is used.

LIST OF REFERENCE SIGNS

101 . . . transport line, 102 . . . rotor, 103 . . . reagent disk, 104 . . . reaction disk, 105 . . . dispensing mechanism, 106 . . . stirring mechanism, 107 . . . spectrometer, 110 . . . specimen container, 111 . . . specimen rack, 112 . . . reaction vessel, 113 . . . reagent container, 114 . . . shield portion, 115 . . . control unit, 201 . . . arm, 202 . . . neutralizing ion, 203 . . . discharge needle, 204 . . . blower fan, 205 . . . neutralization control unit, 206 . . . dispensing position, 207 . . . static electricity, 208 . . . dispensing position, 401 . . . air nozzle, 402 . . . compressed air generation unit, 403 . . . air tube, 404 . . . air pump, 405 . . . compressed air tank, 406 . . . solenoid valve, 601 . . . arm, 602 . . . dispensing probe with neutralizing function, 603 . . . inner cylinder, 604 . . . gap, 605 . . . outer cylinder, 606 . . . inner cylinder tip, 607 . . . liquid level detection control unit, 608 . . . high voltage generator, 609 . . . ground electrode, 610 . . . outer cylinder tip, charge amount measurement unit, 802 . . . analog switch, 803 . . . liquid level detection circuit, 804 . . . charge quantity measurement circuit, 805 . . . control unit, 806 . . . minute voltage, 807 . . . amplifier, 808 . . . A/D converter, 809 . . . specimen container height detector, 810 . . . charge Q, 811 . . . distance d, 812 . . . air with dielectric constant ε, 813 . . . cross-sectional area S, 814 . . . electrostatic capacity C, 901 . . . integrated neutralizing unit, 902 . . . liquid level detection unit, 903 . . . charge quantity measurement unit, 904 . . . high voltage generation unit, 1101 . . . flow A, 1102 . . . travel to dispensing position, 1103 . . . neutralizing operation, 1104 . . . charge quantity measurement, 1105 . . . dispensing operation, 1106 . . . flow B, 1107 . . . flow C

The invention claimed is:

1. An automatic analyzing apparatus comprising:
a spectrometer;
a specimen container configured to accommodate a specimen;
a reaction vessel configured to accommodate a mixture of the specimen and a reagent;
a dispensing mechanism including an arm that holds a probe that aspirates a specimen and discharges the specimen into the reaction vessel, a static eliminator having a generation source of neutralizing ions and a neutralizing ion blowing mechanism configured to blow neutralizing ions generated in the generation source to the specimen container or the reaction vessel; and
a controller connected to the spectrometer and the dispensing mechanism, the controller programmed to:
control the dispensing mechanism to aspirate the specimen from the specimen container at an aspiration position and eject the specimen into the reaction vessel at a dispensing position, and
control the static eliminator to generate neutralizing ions and blow the generated neutralizing ions to the specimen container at the aspiration position before the dispensing mechanism aspirates the specimen to thereby neutralize the specimen container and to blow neutralizing ions to the specimen container reaction vessel at the dispensing position to thereby neutralize the reaction vessel,
wherein the generation source is connected to the probe and allows the probe to generate the neutralizing ions,
wherein the probe includes an inner tube for aspirating the liquid and an outer tube that surrounds the inner tube,
wherein the neutralizing ion blowing mechanism is an outer tube that blows the compressed air generated from the compressed air generation unit, and
wherein the compressed air generated from the compressed air generation unit blows the neutralizing ions generated in the probe to an object via the outer tube.

2. The automatic analyzing apparatus according to claim 1, further comprising:
a neutralization control unit that controls the generation source and the neutralizing ion blowing mechanism,
wherein the control unit is further programmed to:
control the dispensing mechanism to move vertically and horizontally,
control the neutralization control unit to neutralize the specimen container that contains the specimen before the dispensing mechanism moves down, and stops at least the neutralizing ion blowing mechanism while the dispensing mechanism is moving down, and
control the probe to aspirate the specimen while the neutralizing ion blowing mechanism is stopped.

3. The automatic analyzing apparatus according to claim 1,
  wherein the neutralizing ion blowing mechanism includes one of a blower fan and an air tube that blows compressed air generated from a compressed air generation unit.

4. The automatic analyzing apparatus according to claim 1,
  wherein the dispensing mechanism includes a charge amount measurement unit that measures an amount of electric charge on the specimen container in a non-contact manner with the use of the probe.

5. The automatic analyzing apparatus according to claim 4, wherein the probe includes a fluid level detector.

6. The automatic analyzing apparatus according to claim 4, wherein the controller is further programmed to:
  adjust the amount of neutralizing ions to be blown according to a charge amount measured by the charge amount measurement unit.

7. The automatic analyzing apparatus according to claim 5,
  wherein the control unit is programmed to:
  control the charge amount measurement unit to measure the amount of electric charge charged in the specimen container, and control the air blowing to the specimen container by the neutralizing ion blowing mechanism before the liquid level measurement of the specimen contained in the specimen container is performed with the use of the probe.

8. The automatic analyzing apparatus according to claim 7, further comprising a display,
  wherein the controller is programmed to: display a function of at least one of the liquid level detector, a charge amount measurement, and a neutralization in the probe to be selected by a user.

* * * * *